(12) United States Patent
Staniforth

(10) Patent No.: US 6,475,523 B1
(45) Date of Patent: Nov. 5, 2002

(54) POWDERS COMPRISING ANTI-ADHERANT MATERIALS FOR USE IN DRY POWDER INHALERS

(75) Inventor: John Nicholas Staniforth, Bath (GB)

(73) Assignee: Vectura Limited (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/000,065

(22) PCT Filed: Jul. 24, 1996

(86) PCT No.: PCT/GB96/01783

§ 371 (c)(1),
(2), (4) Date: Jun. 16, 1998

(87) PCT Pub. No.: WO97/03649

PCT Pub. Date: Feb. 6, 1997

(30) Foreign Application Priority Data

Jul. 24, 1995 (GB) .............................................. 9515182

(51) Int. Cl.⁷ .............................. A61K 9/00; A61K 9/14
(52) U.S. Cl. ........................... 424/489; 424/45; 424/46; 514/951
(58) Field of Search .............................. 424/46, 47, 45, 424/489, 951, 826; 128/203.15

(56) References Cited

U.S. PATENT DOCUMENTS

| | | | |
|---|---|---|---|
| 6,019,968 A | 2/2000 | Platz et al. ............... | 424/130.1 |
| 6,051,256 A | 4/2000 | Platz et al. ............... | 424/489 |
| 6,153,224 A * | 11/2000 | Staniforth | |
| 6,221,338 B1 * | 4/2001 | Staniforth | |
| 6,309,671 B1 | 10/2001 | Foster et al. ............... | 424/489 |
| 6,358,530 B1 | 3/2002 | Eljamal et al. ............. | 424/488 |
| 6,360,743 B1 | 3/2002 | Andersson et al. .... | 128/203.15 |

FOREIGN PATENT DOCUMENTS

| | | | |
|---|---|---|---|
| GB | 905723 | | 9/1962 |
| GB | 1230087 | | 4/1971 |
| GB | 1381872 | | 1/1975 |
| GB | 2 269 992 | | 3/1994 |
| SA | 9 400 155 | | 7/1995 |
| WO | 91/11173 | * | 8/1991 |
| WO | 91/14422 | * | 10/1991 |
| WO | 92/08447 | * | 5/1992 |
| WO | 94/13271 | * | 6/1994 |
| WO | 95/00127 | * | 1/1995 |
| WO | WO 95/00127 | | 1/1995 |
| WO | WO 95/00128 | | 1/1995 |
| WO | 95/00128 | | 1/1995 |
| WO | 96/234485 | | 8/1996 |
| WO | WO 96/234485 | | 8/1996 |
| ZA | 9 400 155 | | 7/1995 |

* cited by examiner

Primary Examiner—Thurman K. Page
Assistant Examiner—Brian K. Seidleck
(74) Attorney, Agent, or Firm—Davidson, Davidson & Kappel, LLC

(57) ABSTRACT

A powder for use in a dry powder inhaler comprises active material and additive material. The additive material comprises an anti-adherent material and the powder includes at least 60% by weight of active material. The inclusion of the additive material in the powder has been found to give an increased respirable fraction of the active material.

24 Claims, 1 Drawing Sheet

POWDERS COMPRISING ANTI-ADHERANT MATERIALS FOR USE IN DRY POWDER INHALERS

BACKGROUND OF THE INVENTION

This application is a 371 of PCT/GB96/01783, filed Jul. 24, 1996.

This invention relates to powders for use in dry powder inhalers.

BRIEF SUMMARY OF THE INVENTION

Inhalers are well known devices for administering pharmaceutical products to the respiratory tract by inhalation. Inhalers are widely used particularly in the treatment of diseases of the respiratory tract.

There are a number of types of inhaler currently available. The most widely used type is a pressurised metered dose inhaler (MDI) which uses a propellant to expel droplets containing the pharmaceutical product to the respiratory tract. Those devices are disadvantageous on environmental grounds as they often use CFC propellants, and on clinical grounds related to the inhalation characteristics of the devices.

An alternative device to the MDI is the dry powder inhaler. The delivery of dry powder particles of pharmaceutical products to the respiratory tract presents certain problems. The inhaler should deliver the maximum possible proportion of the active particles expelled to the lungs, including a significant proportion to the lower lung, preferably at the low inhalation capabilities to which some patients, especially asthmatics, are limited. It has been found, however, that, when currently available dry powder inhaler devices are used, in many cases only about 10% of the active particles that leave the device on inhalation are deposited in the lower lung. More efficient dry powder inhalers would give clinical benefits.

The type of dry powder inhaler used is of significant importance to the efficiency of delivery over a range of airflow conditions of the active particles to the respiratory tract. Also, the physical properties of the powder used affect both the efficiency and reproducibility of delivery of the active particles and the site of deposition in the respiratory tract.

On exit from the inhaler device, the active particles should form a physically and chemically stable aerocolloid which remains in suspension until it reaches a conducting bronchiole or smaller branching of the pulmonary tree or other absorption site preferably in the lower lung. Once at the absorption site, the active particle should be capable of efficient collection by the pulmonary mucosa with no active particles being exhaled from the absorption site.

The size of the active particles is particularly important. For effective delivery of active particles deep into the lungs, the active particles should be small, with an equivalent aerodynamic diameter substantially in the range of 0.1 to 5 μm, approximately spherical and monodispersed in the respiratory tract. Small particles are, however, thermodynamically unstable due to their high surface area to volume ratio, which provides significant excess surface free energy and encourages particles to agglomerate. In the inhaler, agglomeration of small particles and adherence of particles to the walls of the inhaler are problems that result in the active particles leaving the inhaler as large stable agglomerates or being unable to leave the inhaler and remaining adhered to the interior of the inhaler.

The uncertainty as to the extent of formation of stable agglomerates of the particles between each actuation of the inhaler and also between different inhalers and different batches of particles, leads to poor dose reproducibility.

In an attempt to improve that situation, dry powder for use in dry powder inhalers often include coarse carrier particles mixed with fine particles of active material. The active particles adhere to the surfaces of the carrier particles whilst in the inhaler device, and are dispersed on inhalation into the respiratory tract to give a fine suspension. The carrier particles are often large particles greater than 90 μm in diameter to give good flow properties because small particles with a diameter of less than 10 μm may become coated on the wall of the delivery device and have poor flow and entrainment properties leading to poor dose uniformity.

There are, however, problems associated with the addition of carrier particles to the active particles in the dry powder, for example problems related to the efficient release of the active particles from the surfaces of the carrier particles on inhalation. Furthermore, in some cases it is preferred for no carrier particles to be present in the powder administered.

In known dry powder inhaler devices, doses of powder containing only active particles are dispensed. The powder contains no carrier particles or other additives and the amount of powder in each dose is small, usually less than 1 mg. The volume of the dose may be, for example, approximately 6.5 μl.

Problems involved in dispensing a powder containing only particles of active material include (i) formation of stable agglomerates of the small particles which often are not broken down into individual particles in the airstream when the particles are inhaled and are, therefore, less likely to reach the lower lung on inhalation of the powder than the fine individual active particles;

(ii) variations in the amount of powder metered from a reservoir of the inhalation device due to poor flow properties of the powder and inconsistent agglomeration, leading to inconsistency in the size of dose, which may vary as much as ±50% compared with the nominal dose for the device;

(iii) incomplete removal of the dose from the device due to adherence of the particles to the walls of the device, leading to poor dose reproducibility.

An object of the present invention is to provide a dry powder for use in dry powder inhalers which overcomes or mitigates at least one of the above disadvantages.

DETAILED DESCRIPTION

Figure 1:
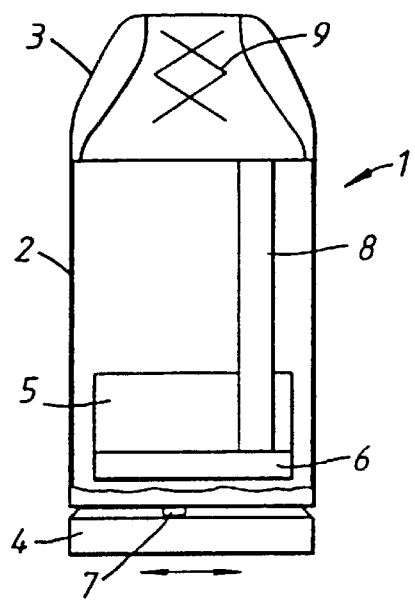
FIG. 1 shows a sectional view of a dry powder inhaler

According to the invention, there is provided a powder for use in a dry powder inhaler, the powder comprising active material and additive material, the additive material comprising an anti-adherant material and the powder including at least 60% by weight of active material based on the weight of the powder.

A purpose of the additive material is to hinder the formation of stable agglomerates of the active material in the powder. As indicated above, stable agglomeration of the active particles with the known powders may lead to decreased deposition of the active material in the lower lung, together with poor dose uniformity. That is because, when the small active particles agglomerate, the agglomerates which are formed may have a diameter of 100 μm or more. If those agglomerates do not break up when the powder is inhaled, they are unlikely to reach the lower lung due to their size.

The addition of the anti-adherent material decreases the cohesion between the particles of the powder containing the active material. It is thought that the additive material interferes with the weak bonding forces, such as Van der Waal's and Coulomb forces, between the small particles, helping to keep the particles separated and may be thought of as weak links or "chain breakers" between the particles. Adhesion of the particles to the walls of the device is also reduced. Where agglomerates of particles are formed, the addition of the additive material decreases the stability of those agglomerates so that they are more likely to break up in the turbulent airstream created on inhalation to form small individual particles which are likely to reach the lower lung.

The reduced tendency of the particles to bond strongly either to each other or to the device itself, reduces powder cohesion and adhesion and promotes better flow characteristics which leads to improvements in the dose reproducibility by reducing the variation in the amount of powder metered out for each dose and improving the release of the powder from the device as well as increasing the likelihood that the active material which does leave the device will reach the lower lung of the patient.

It is thought that it is favourable for unstable agglomerates of particles to be present in the powder when it is in the inhaler device. As indicated above, for a powder to leave an inhaler device efficiently and reproducibly, the particles of such a powder should be large, preferably larger than 45 μm. Such a powder may be in the form of either individual particles having a size of 45 μm or larger and/or agglomerates of finer particles, the agglomerates having a size of 45 μm or larger. The agglomerates formed can have a size of as much as 100 μm and, with the addition of the additive material, those agglomerates are more likely to be broken down efficiently in the turbulent airstream created on inhalation. Therefore the formation of unstable agglomerates of particles in the powder may be favoured compared with a powder in which there is substantially no agglomeration.

The reduction in the cohesion and adhesion between the active particles could lead to equivalent performance with reduced agglomerate size, or even with individual particles.

Where reference is made to anti-adherent materials, the reference is to include those materials which will decrease the cohesion between the particles of the powder. Those materials will include those usually thought of as anti-adherent materials, for example leucine, as well as others, for example, lecithin, which are not generally thought of as being anti-adherent but may nonetheless have the effect of decreasing the cohesion between the particles of the powder. Other materials commonly added to powders for use in inhalers, for example lactose and various other carrier particle materials, are not anti-adherent materials per se but might be added to a powder in addition to a suitable anti-adherent material, for example leucine as indicated below.

Furthermore, many materials are not suitable anti-adherent materials because they are "sticky" and tend to increase cohesion between particles. For example, fatty acids, increase stickiness in powders and are thought to be unsuitable as the additive material. Also, other materials such as sorbitan esters (for example SPAN 85) and cyclo dextrins are not suitable anti-adherent materials.

It is possible that materials which are anti-adherent for one type of active material, will not be anti-adherent for a different type. A suitable test to determine whether or not an additive material is anti-adherent is as follows.

The "Aeroflow" apparatus of Amherst Process Instruments Incorporated of Mountain Farms Technology Park, Hadley, Mass. 01035-9547 U.S.A., is used to assess whether a material is anti-adherent.

The Aeroflow apparatus is used to measure the flow properties of powders. A sample of powder is placed in a perspex cylinder which is rotated at a speed of about 5 rpm about a horizontal axis. As the cylinder rotates, the powder will tend to form a pile of powder which extends around the inner surface of the cylinder as powder material is carried round by the rotating cylinder. When the height of the pile reaches a certain level, powder material from the top of the pile avalanches down towards the bottom of the pile. Thus as the cylinder rotates, the powder will avalanche at a frequency dependent on the properties of the powder. For a freely flowing powder material, the time between avalanches will be low whereas for a cohesive material, the time between avalanches will be great.

The general procedure for the test is as follows:

(a) A powder for testing is made by mixing together active material and additive material as described in (i) or (ii) below to form a powder containing the concentration by weight of additive material of the powder to be tested. The particles of the powder are agglomerated by mixing the particles for 10 minutes at a relative humidity of 55% in a tumbling blender, preferably a Turbula mixer.

(i) Where the additive material is in the form of particles, blend the active and additive materials together, (ii) where the additive material is to form a coating on the surfaces of the active particles as described below, the additive material is added to the active particles from suspension or from solution and the resulting powder is dried and divided.

(b) A 200 g sample of the powder obtained in (a) above is put into the Aeroflow apparatus and the mean time between avalanches is measured as the cylinder is rotated.

(c) (b) above is repeated for a sample of active material which has been prepared as in (a) above except that no additive material is added.

For a material which is to be taken as an anti-adherent material for the purposes of this invention, the mean time between avalanches will be lower for the material containing the additive material, indicating improved flow properties and less cohesion.

For additive materials comprising a fatty acid, the time between avalanches is greater when the fatty acid has been added to the material. Thus fatty acids are unsuitable for use as the anti-adherent material.

Where it is indicated that a material is not anti-adherent, that material might be added to the active material, for example as a diluent, provided that a suitable anti-adherent additive material is also added such that the resulting effect of the additive material and the diluent is anti-adherent. Where further components other than the active material and the anti-adherent material are included in the powder, advantageously the complete powder also "passes" the above test in that the combined effect of all of the components added to the active material is that of an anti-adherent material.

Advantageously, the powder comprises at least 70%, more preferably at least 80% by weight of active material based on the weight of the powder. Most advantageously, the powder comprises at least 90%, more preferably at least 95%, more preferably at least 97%, by weight of active material based on the weight of the powder. It is believed that there are physiological benefits in introducing as little powder as possible to the lungs, in particular material other than the active ingredient to be administered to the patient. Therefore, the quantities in which the additive material is added are preferably as small as possible. The most preferred powder, therefore, would comprise more than 99% by weight of active material.

Advantageously, at least 90% by weight of the particles of the powder have a particle size less than 63 $\mu$m, preferably less than 30 $\mu$m and more preferably less than 10 $\mu$m. As indicated above, the size of the particles of the powder should be within the range of about from 0.1 $\mu$m to 5 $\mu$m for effective delivery to the lower lung. Where the additive material is in the form of particles of material, as is described below, it may be advantageous for particles of the additive material to have a size outside the preferred range for delivery to the lower lung.

As indicated above, in some cases it will be preferred for the particles to be in the form of agglomerates in the powder. In such cases, the particle sizes indicated above are those of the individual particles making up the agglomerates.

It will be appreciated that the chemical composition of the additive material is of particular importance.

Advantageously, the additive material comprises physiologically acceptable material. Clearly, it is highly preferable for the additive material to be a material which may be safely inhaled into the lower lung, where it would usually be absorbed into the blood stream. The additive material should therefore be one which is safe to administer by inhalation. The additive material may include a combination of one or more materials.

Advantageously, the additive material includes one or more compounds selected from amino acids and derivatives thereof, and peptides and polypeptides having a molecular weight of between about 0.25 to 1000 kDa, and derivatives thereof. Amino acids, peptides and polypeptides and their derivatives are physiologically acceptable and act as anti-adherent materials when added to the active material. It is particularly advantageous for the additive material to comprise an amino acid. Amino acids have been found to give, when present as additive material, high respirable fraction of the active material and also good flow properties of the powder. A preferred amino acid is leucine, in particular L-leucine. Whilst the L-form of the amino acids is preferred in the Examples, the D- and DL-forms may also be used. The additive material may comprise one or more of any of the following amino acids: leucine, isoleucine, lysine, valine, methionine, cysteine, phenylalanine.

As indicated above, the additive material may include derivatives of amino acids or peptides. For example the additive material may be a salt or an ester, for example aspartame, or may be N acetyl-L cysteine. The additive material may comprise salts such as acesulfame K or other sweeteners, for example saccharin sodium or a cyclamate.

The additive material may include one or more water soluble compounds. Those compounds, if they penetrate into the deep lung may therefore be absorbed into the blood stream, which is advantageous.

The additive material may include one or more surface active materials which may be water soluble, for example, lecithin, in particular soya lecithin. Lecithin is not an especially preferred additive material because it is thought that at least in some cases it could give increased cohesion in the powder material.

The additive material may include dipolar ions which may be zwitterions.

Advantageously, the additive material includes a glidant material. A glidant material is one that will decrease the resistance to sliding of the particles. The addition of a glidant material, therefore, will lead to improved release of the powder from the inhaler device and therefore better dose uniformity. The glidant materials which have this effect will include those usually thought of as glidants as well as those not usually thought of as glidants but which have a glidant effect when added to the active material. Many of the anti-adherent materials described above are also glidants. The glidant material may, therefore, be the same compound as that of the anti-adherent material, or may be a different compound or a mixture of compounds.

The active material referred to throughout the specification will be material comprising one or a mixture of pharmaceutical products. It will be understood that the term "active material" includes material which is biologically active, in the sense that it is able to decrease or increase the rate of a process in a biological environment. The pharmaceutical products include those products which are usually administered orally by inhalation for the treatment of disease such as respiratory disease e.g. β-agonists, salbutamol and its salts or salmeterol and its salts. Other pharmaceutical products which could be administered using a dry powder inhaler include peptides and polypeptides, such as DNase, leucotrienes and insulin.

The active material may include a $\beta_2$-agonist, which may include salbutamol, a salt of salbutamol or a combination thereof. Salbutamol and its salts are widely used in the treatment of respiratory disease. The active material may be salbutamol sulphate. The active material may be terbutaline, a salt of terbutaline, for example terbutaline sulphate, or a combination thereof. Terbutaline sulphate is of particular importance. The active material may be ipatropium bromide.

The active material may include a steroid, which may be beclomethasone dipropionate or may be fluticasone. The active material may include a cromone which may be sodium cromoglycate or nedocromil or its salts. The active material may include a leukotriene receptor antagonist.

The active material may include a carbohydrate, for example heparin.

Advantageously, the powder comprises particles of active material and particles of additive material. Where particles of additive material are used, by choosing a particular size of the additive particles, as described below, the amount of additive material entering the lower lung may be minimised. Also, it may be preferable for the additive to be present in the powder as particles rather than, for example, a coating around the particles of active material which may hinder the absorption of the active material into the blood stream.

Advantageously, at least 90% by weight of the additive particles have a particle size less than 63 μm, preferably, less than 30 μm, and more preferably less than 10 μm. The additive particles will usually have a particle size slightly larger than the particle size of the active particles to encourage deposition of the additive particles in the upper airways. To restrict the amount of the additive material penetrating to the deep lung on inhalation, it is advantageous to include additive particles having a size greater than 5 μm. The size of the particles may be calculated by laser diffraction or other method by which the aerodynamic diameter of the particles can be determined.

The additive particles may be non-spherical in shape. The additive particles may be plate-like particles, for example leucine particles. Alternatively the additive particles may be angular, for example prisms, or dendritic in shape, for example aspartame particles. Plate-like particles may give improved surface interaction and glidant action between the surfaces of the active particles thereby decreasing bonding between the active particles and reducing stable agglomeration.

Alternatively, for example where the nature of the additive material is such that small particles are not easily formed, or for clinical reasons, the additive material may form at least a partial coating on the surfaces of particles of the active material. It is found that even when a large amount of the additive material is added to the active material, there is no "coating" of the active particles in the sense in which that word would normally be used in the art, namely to refer to a continuous envelope around the active particle. Instead, a discontinuous covering is formed on the active particle. It is believed that the presence of such a discontinuous covering, as opposed to a "coating" is an important and advantageous feature of the present invention.

Additive material may be present in the powder both in the form of small particles and in the form of a coating on the surfaces of the particles of active material.

Where the additive material is to form a coating on the surfaces of the particles of active material, the additive material may be added to the active material from a suspension or from solution. The additive material may be added to the active material by co-crystallisation, co-spray drying, co-granulation or other similar method.

Where the additive is in the form of particles, the powder may be produced by, for example, blending together micronised active material and micronised additive material. Alternatively, the components of the powder may be micronised together to form the powder material.

The ratio in which the additive material and the active material are present in the powder will depend on the type of inhaler device used, the type of active material used and the required dose. Usually, the powder comprises at least 0.1% by weight of additive material based on the weight of the powder. The powder preferably comprises between about 0.1% and 40%, more preferably between about 0.25% and 5% by weight of additive material based on the weight of the active material.

It has been found that the addition of more additive material does not necessarily give a greater improvement in the properties of the resulting powder. For example, in the case where the additive material is leucine as in Example 8 below, the addition of 1% by weight of leucine gives good results, but the addition of 5% or 10% by weight of leucine does not give better results, indeed the respirable fraction is seen to decrease with increased addition of leucine.

Furthermore, because the additive material will in many cases be inhaled into the lung, it is preferable for only a small amount of additive material to be added.

The optimum amount of additive material in the powder will depend on the active material and additive material used. Advantageously, the powder comprises not more than 8% by weight, preferably not more than 5% by weight, of additive material. In some cases it will be advantageous for the powder to contain about 1% by weight of additive material.

Advantageously, at least 95% by weight of the active particles have a particle size less than 10 $\mu$m. Preferably, at least 95% by weight of the active particles have a particle size between about 0.1 $\mu$m and 10 $\mu$m, more preferably between about 0.1 $\mu$m and 5 $\mu$m. The particles will therefore give a good suspension on release from the inhaler device and delivery of the active particles deep into the respiratory tract. The size of the particles may be calculated as described above in respect of the additive particles.

The powder may also contain, for example, flavourings and colourant materials and may also contain diluents. Advantageously the powder includes less than 20% preferably less than 10%, more preferably less than 1%, by weight of constituents other than the active material and the anti-adherent material.

According to the invention, there is also provided a powder for use in a dry powder inhaler the powder comprising active particles and additive material, at least 90% by weight of the powder particles having a particle size of less than 63 μm, the powder including at least 60% by weight of active particles based on the weight of the powder.

Advantageously, at least 90% by weight of the powder particles have a particle size of less than 30 μm, preferably less than about 10 μm. Advantageously, the powder includes at least 80%, preferably at least 90% by weight of active particles based on the weight of the powder.

Advantageously, the powder includes not more than 8%, more advantageously not more than 5% by weight of additive material based on the weight of the powder. As indicated above, in some cases it will be advantageous for the powder to contain about 1% by weight of additive material.

As indicated above, the additive material may be in the form of particles.

The invention also provides, a powder for use in a dry powder inhaler, the powder comprising active particles and additive material, the additive material forming at least a partial coating on the surfaces of the particles of active material, the powder including at least 60% by weight of active material based on the weight of the powder, at least 90% by weight of the particles of the powder having a particle size less than 63 μm.

Advantageously, the powder includes at least 80%, preferably at least 90% by weight of active material based on the weight of the powder.

According to the invention, there is also provided a dry powder inhaler including a powder as described above.

Advantageously, the inhaler may be activated to dispense a dose of less than 10 mg of the powder, preferably not more than 5 mg, more preferably not more than 1 mg. Obviously, the size of the dose will depend on the active material to be delivered and the inhaler device used.

The invention also provides a dose of powder, the dose containing not more than 5 mg of powder described above, more preferably not more than 1 mg of the powder.

The invention also provides the use of an anti-adherent additive material in a powder for use in a dry powder inhaler, for improving the flow characteristics of the powder, the powder comprising at least 60% by weight of active material based on the weight of the powder. The test to assess whether a material is an anti-adherent material is indicated above.

Unless it is clear from the context otherwise, where reference is made to a range of sizes of particles, and to the size of particles, it is to mean that the majority of the relevant particles are within that range or are of that size. Preferably at least about 90% by weight of the relevant particles will be in that range or be of that size, more preferably at least 95% by weight.

The size of particles may, where appropriate be selected and/or measured using a sieving method. Otherwise, the size of the particles may be determined using laser light diffraction, or other method in which the aerodynamic diameter of the particles may be determined, for example microscopic image analysis.

One of the objects of the invention is to hinder the formation of stable agglomerates of particles, especially active particles, in the powder. However, as described above, it may be desirable for unstable agglomerates to be formed in the powder, and the size of those agglomerates may be as large as 100 μm or more. The size of particles in the powder, when considering the agglomerates, is to be taken as the size of the individual particles making up the agglomerate. The sizes of the individual particles may be determined using microscopic image analysis.

Embodiments of the invention will now be described by way of example with reference to the accompanying drawings of which:

FIG. 1 shows a view of a dry powder inhaler device known as a Turbohaler (Trade Mark). The Turbohaler is a breath actuated inhaler which may be used to meter out and deliver small quantities of dry powder. The mass of powder delivered for each inhalation is often less than 1 mg.

As shown in FIG. 1, the Turbohaler comprises an outer cylindrical body 2 which has a mouthpiece 3 around one end and a rotatable base 4 at the other end. The body 2 houses a storage chamber 5 for storing the dry powder to be dispensed, and a dosing disc 6 under the storage chamber. The dosing disc 6 includes a number of identical cavities around its edge.

Rotation of the base 4 causes rotation of the disc 6 and the cavities pass under the storage chamber 5 and are filled with a volume of the dry powder material. Forcible filling of the cavities, in an attempt to reduce variability in the amount of powder filled into the cavities, is achieved by the provision of scrapers above the cavities and a pressure plate below the dosing disc urging the disc 6 towards the storage chamber 5. The base 4 is rotated backwards and forwards to dispense the powder into the cavities.

Rotation of the disc 6 also brings successive cavities in and out of communication with a channel 8 which leads from the disc 6 to the mouthpiece 3.

To administer the powder, a filled cavity is brought into alignment with the channel 8 and a patient inhales through the mouthpiece 3. Air is drawn into the body via an inlet 7 (and other inlets) and the air passes through a hole in the pressure plate and through holes in the bottom of the cavity thereby discharging the contents of the cavity into the channel 8. The powder is inhaled via the mouthpiece 3.

To increase the turbulent airflow in the device, to help break up any agglomerates of powder, the device includes other inlets in the body 2. The mouthpiece includes channels 9 to increase turbulence.

The storage chamber usually has the capacity to hold approximately 200 doses of the powder and, when empty, may be refilled or disposed of.

DETAILED DESCRIPTION OF THE PREFERRED EMBODIMENTS

Examples of suitable powders according to the invention, which may be used in a Turbohaler are as follows. Whilst the Examples refer to use of the powders in a Turbohaler, powders according to the invention may instead be used in other suitable devices, for example, a MIAT-Haler.

EXAMPLE 1

2 g leucine powder was mixed with 198 g terbutaline sulphate powder in a Turbula mixer for approximately 15 minutes. Before mixing, the particles of the terbutaline sulphate had a mass median aerodynamic diameter (MMAD) of 2.1 μm, and 95% by weight of the leucine powder had a particle size less than 150 μm (at least 95% by weight passes through a 150 μm mesh sieve).

The resulting powder was agglomerated using a milling procedure. 50 g samples of the powder were milled in a porcelain ball mill (manufactured by Pascall Engineering Company) having a diameter of approximately 150 mm, using steel grinding balls. The milling was continued for about 6 hours. The agglomerated powder was filled into a Turbohaler in a known way.

Each metered dose for inhalation from the Turbohaler contained approximately:

| | |
|---|---|
| 500 μg | terbutaline sulphate |
| 5 μg | leucine. |

An approximate value for the volume of the metered dose might be 6.5 μl.

EXAMPLE 2

2 g leucine powder was mixed with 198 g terbutaline sulphate powder as described in Example 1. The powder mixture was filled into a Turbo-haler.

Each metered does for inhalation from the Turbohaler contained approximately

| | |
|---|---|
| 500 μg | terbutaline sulphate |
| 5 μg | leucine |

An approximate value for the volume of the metered dose might be 6.5 μl.

EXAMPLE 3

4 g of leucine powder was mixed with 196 g terbutaline sulphate powder as described above for Example 1. The resulting powder was agglomerated using a milling procedure as described for Example 1 and filled into a Turbohaler.

Each metered dose for inhalation from the Turbohaler contained approximately

| | |
|---|---|
| 500 μg | terbutaline sulphate |
| 10 μg | leucine |

EXAMPLE 4

1 g soy lecithin (95% by weight of particles less than 710 μm) was dissolved in 10 g water and 10 g IMS (or in 20 g 95% ethanol) and added to 199 g terbutaline sulphate powder (MMAD 2.1 μm) in a high shear mixer. The mixture was blended for four minutes and then dried on trays at 40° C. for 6 hours. The powder was screened through a 500 μm sieve then milled in a ball mill using steel balls, as described for Example 1, for six hours to cause agglomeration.
The agglomerated powder was filled into a Turbohaler.

Each metered dose for inhalation from the Turbohaler contained approximately

| | |
|---|---|
| 500 μg | terbutaline sulphate |
| 2.5 μg | soy lecithin |

EXAMPLE 5

Agglomerated powder was prepared as for Example 3 above except that 4 g soy lecithin (95% by weight of particles less than 710 μm) was dissolved in 10 g water and 10 g IMS and added to 196 g terbutaline sulphate powder (MMAD 2.1 μm). The agglomerated powder was filled into a Turbohaler.

Each metered dose for inhalation from the Turbohaler contained approximately

| | |
|---|---|
| 500 μg | terbutaline sulphate |
| 10 μg | soy lecithin |

EXAMPLE 6

1 g solid state soy lecithin having 95% by weight of particles having a size less than 100 μm were added to 199 g terbutaline sulphate (MMAD 2.1 μm) and mixed in a Turbula mixer for approximately 15 minutes. The resulting powder was agglomerated by ball milling as described in Example 1. The agglomerated powder was filled into a Turbohaler.

Each metered dose for inhalation from the Turbohaler contained approximately

| | |
|---|---|
| 500 μg | terbutaline sulphate |
| 2.5 μg | soy lecithin |

EXAMPLE 7

A powder for inhalation using a Turbohaler was prepared by mixing 199 g budesonide and 1 g L-leucine as described above for Example 1. The powder was agglomerated as described for Example 1 and filled into the Turbohaler in a known way.

Each metered dose for inhalation from the Turbohaler contained approximately:

| | |
|---|---|
| 100 μg | budesonide |
| 0.5 μg | L-leucine |

It will be understood that the Turbohaler device described above is only an example of a dry powder inhaler device which may be used to dispense powder according to the invention, and that different dry powder inhaler devices may be used.

The efficiency of the delivery of the active particles to the lungs of a patient by the inhaler device, and the dose reproducibility achieved, may be assessed using a twin stage impinger (TSI) as described below.

Figure 2:
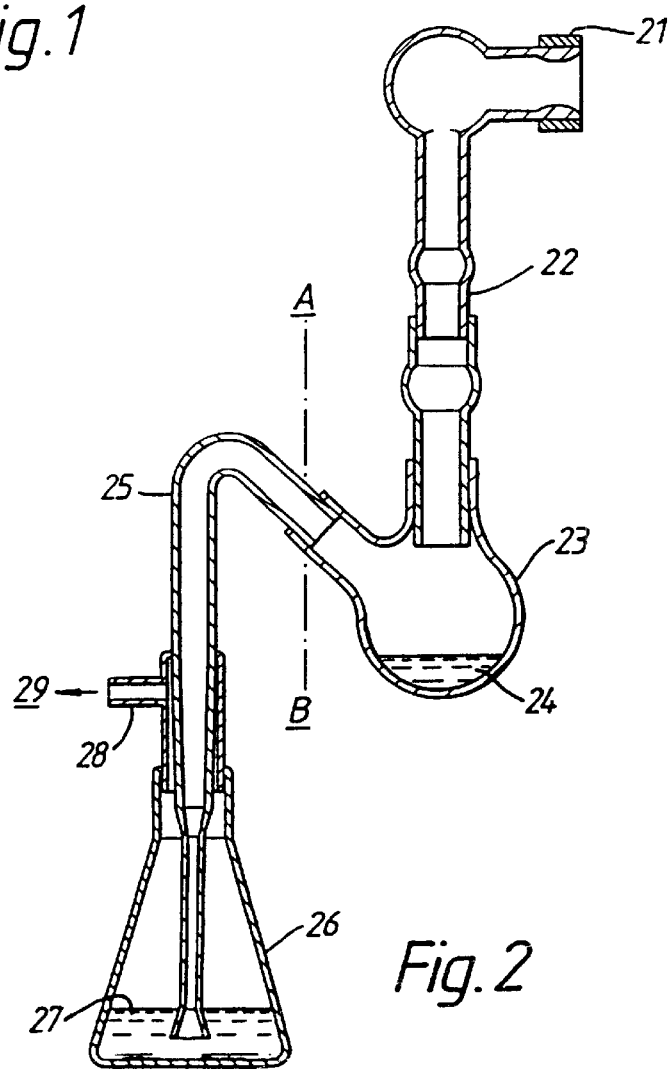
FIG. 2 is a sectional diagram of a twin stage impinger

FIG. 2 shows a diagrammatic arrangement of a TSI.

The TSI is a two stage separation device used in the assessment of oral inhalation devices. Stage one of the apparatus is shown to the right of the line AB in FIG. 2 and is a simulation of the upper respiratory tract. To the left of that line is stage two which is a simulation of the lower respiratory tract.

The TSI comprises a mouth 21 which comprises a polydimethylsiloxane adaptor, moulded to accept the mouthpiece of the inhaler device, upper tubing 22 and upper impinger 23 to simulate the upper respiratory tract, the upper impinger containing liquid 24, and lower tubing 25 and lower impinger 26 to simulate the lower respiratory tract, the lower impinger containing liquid 27. The lower impinger 26 is connected via an outlet pipe 28 to a pump 29 which draws air through the TSI apparatus at a predetermined rate. The base of the lower tubing 25 is at the level of the liquid 27 such that all the air drawn through the TSI bubbles through the lower liquid 27. The liquid used in both the upper and lower impinger is distilled water.

In use, the inhaler is placed in a mouth 21 of the TSI. Air is caused to flow through the apparatus by means of a pump 29 which is connected to stage two of the TSI. Air is sucked through the apparatus from the mouth 21, flows through upper tubing 22 via the upper impinger 23 and the lower tubing 25 to the lower impinger 26 where it bubbles through liquid 27 and exits the apparatus via outlet pipe 28. The liquid 24 in the upper impinger 23 traps any particle with a size such that it is unable to reach stage two of the TSI. Fine particles, which are the particles able to penetrate to the lungs in the respiratory tract, are able to pass into stage two of the TSI where they flow into the lower impinger liquid 27.

30 ml of distilled water is put into the lower impinger 26 and 7 ml of distilled water is put into the upper impinger 23. The lower tubing 25 is arranged such that its lower end is at the level of the water in the lower impinger 26. The pump 29 is adjusted to give an air flow rate of 60 liters per minute in the apparatus.

The Turbohaler inhaler device is weighed. The mouthpiece 3 of the inhaler is connected to the mouth 21 of the TSI, the base 4 is rotated to dispense a dose of powder and the pump is switched on and timed for a period of ten seconds. The pump is then switched off and the Turbohaler is removed from the TSI, reweighed and the amount of powder lost from the inhaler calculated.

The sections of the apparatus making up stage one of the TSI are washed into a second flask and made up to 250 ml with distilled water. The sections making up the second stage of the TSI are washed into a third flask and made up to 100 ml with distilled water.

The test is repeated several times to assess the dose reproducibility.

The amount of active substance in each section of the TSI is measured for each test. For example, when the active substance is budesonide as for the Examples below, the following method may be used.

The contents of the flasks containing the washing from the stages of the TSI are assayed using High Performance Liquid Chromatography (HPLC) analysis for the content of budesonide and compared against standard solutions containing 0.5 μg/ml and 1 μg/ml of budesonide.

The percentage of budesonide in each stage of TSI is calculated from the standard response for each test and the mean for the tests may be calculated to give an indication of the proportion of the active particles reaching the second stage of the TSI apparatus and therefore an indication of the proportion of active substance which would reach the lower lung of a patient.

The variation in the measured values for the tests gives an indication of the dose reproducibility for the inhaler and the dry powder used.

EXAMPLE 8

Micronised budesonide was blended with micronised L-leucine to produce a powder by the following method.

Budesonide and L-leucine were mixed to give a concentration of 1% by weight of leucine and the mixture was blended in a Turbula mixer for up to 30 minutes. The blend was passed through a 355 μm aperture diameter sieve to improve mixing and to break up stable agglomerates to produce a powder having loose agglomerates of particles.

The resulting powder was weighed and filled into a Turbohaler inhaler device such that each actuation of the device dispensed about 200 μg of powder.

The above method was repeated to produce powders having 5% by weight of leucine and 10% by weight of leucine.

The efficiency of the delivery of the active material for the powders by the inhaler was then assessed using the TSI as described above.

Table 1 below shows the results of the TSI testing for each of the different percent by weight of leucine. The respirable fraction is calculated as the percentage of the total amount of drug emitted from the device that reaches stage two of the TSI and gives an indication of the proportion of active particles which would reach the deep lung in a patient. The standard deviation and the coefficient of variation are also given.

TABLE 1

|  | 1% leucine | 5% leucine | 10% leucine |
| --- | --- | --- | --- |
| Respirable fraction (%) | 67.3 | 59.1 | 54.9 |
| Standard deviation (%) | 2.2 | 6.8 | 4.8 |
| Coefficient of variation (%) | 3.3 | 11.6 | 8.7 |

Where no leucine is added to the active powder, the respirable fraction is about 55%.

In addition, it will be seen that the coefficient of variation is low, especially for the powder containing 1% by weight of leucine indicating good reproducibility of the results (corresponding to improved dose uniformity of the administered drug). This indicates that the dose uniformity is also significantly better than for the currently commercially available Turbohaler product in which the powder composition does not contain the leucine additive material.

EXAMPLE 9

A powder was made by the method of Example 8, by blending micronised budesonide and 5% by weight of micronised L-leucine and 15% by weight of Sorbolac (a lactose powder having a particle size less than 63 μm of Meggle Milchindustrie, Reitmehring Germany).

The resulting powder was assessed using the TSI.

Table 2 below shows the results of the TSI testing including the respirable fraction, the standard deviation and the coefficient of variation.

TABLE 2

|  | 5% leucine and 15% lactose |
| --- | --- |
| Respirable fraction (%) | 74.0 |
| Standard deviation (%) | 3.1 |
| Coefficient of variation (%) | 4.2 |

It can be seen that the addition of the lactose diluent significantly increased the respirable fraction and improved the dose uniformity.

What is claimed is:

1. A powder for use in a dry powder inhaler, the powder comprising active material and additive material, the additive material comprising an anti-adherent material including one or more compounds selected from amino acids and derivatives thereof, and peptides and polypeptides having a molecular weight of between about 0.25 to 1000 kDa, and derivatives thereof, and the powder including at least 60% by weight of active material based on the weight of the powder and further including not more than 10% by weight of additive material based on the weight of the powder, in which at least 90% by weight of the powder particles have a particle size of less than 63 μm.

2. A powder according to claim 1, wherein the additive material forms at least a partial coating on the surfaces of particles of the active material.

3. A powder according to claim 1, wherein the additive material includes an amino acid.

4. A powder according to claim 1, wherein the powder comprises at least 80% by weight of active material based on the weight of the powder.

5. A powder according to claim 1, wherein at least 90% by weight of the particles of the powder have a particle size less than 10 μm.

6. A powder according to claim 1, wherein the additive material includes leucine.

7. A powder according to claim 1, wherein the additive material includes one or more water soluble compounds.

8. A powder according to claim 1, wherein the additive material includes dipolar ions.

9. A powder according to claim 1, wherein the additive material includes zwitterions.

10. A powder according to claim 1, wherein the additive material includes greater than a glidant material.

11. A powder according to claim 1, wherein the active material includes a $B_2$-agonist.

12. A powder according to claim 1, wherein the powder comprises particles of active material and particles of additive material.

13. A powder according to claim 1, wherein the powder comprises at least 0.1% by weight of additive material on the weight of the powder.

14. A powder according to claim 1, wherein the powder comprises not more than 5% by weight of additive material based on the weight of the powder.

15. A powder according to claim 1, wherein at least 95% by weight of the active particles have a particle size of less than 10 μm.

16. A powder according to claim 1, wherein at least 95% by weight of the active particles have a particle size between about 0.1 μm and 5 μm.

17. A powder according to claim 1, wherein the powder includes less than 20% by weight of constituents other than the active material and the anti-adherent material.

18. A powder for use in a dry powder inhaler the powder comprising a $\beta_2$-agonist as an active material and additive material comprising an anti-adherent material selected from leucine, L-leucine, D-leucine, DL-leucine, isoleucine, valine, methionine, cysteine, phenylalanine, and mixtures thereof, at least 95% by weight of the powder particles having a particle size of less than 10 μm, the powder including at least 60% by weight of active materials based on the weight of the powder, and further including not more than 10% by weight of additive material based on the weight of the powder.

19. A powder according to claim 18, wherein at least 90% by weight of the powder particles have a particle size of less than 30 μm.

20. A powder according to claim 18, wherein the powder includes at least 80% by weight of active particles based on the weight of the powder.

21. A powder according to claim 18, wherein the powder includes not more than 5% by weight of additive material based on the weight of the powder.

22. A dry powder inhaler including a powder comprising an active material, and an additive material, the additive material comprising an anti-adherent material selected from lecithin, leucine, L-leucine, D-leucine, DL-leucine, isoleucine, valine, methionine, cysteine and phenylalanine, and the powder including at least 60% by weight of active material based on the weight of the powder and further including not more than 40% by weight of additive material based on the weight of the powder, in which at least 95% by weight of the active particles have a particle size less than 10 μm.

23. A dry powder inhaler according to claim 22, wherein the powder inhaler comprises not more than 10% by weight of additive material based on the weight of the powder.

24. A dry powder inhaler according to claim 22, wherein at least 95% by weight of the powder particles have a particle size of less than 10 μm.

* * * * *